United States Patent [19]

Glazer

[11] Patent Number: 5,552,387
[45] Date of Patent: Sep. 3, 1996

[54] POLYCYCLIC ETHER ANTIBIOTICS

[75] Inventor: Edward A. Glazer, Waterford, Conn.

[73] Assignee: Pfizer Inc., New York, N.Y.

[21] Appl. No.: 284,874

[22] Filed: Aug. 2, 1994

Related U.S. Application Data

[63] Continuation of Ser. No. 804,482, Dec. 9, 1991, abandoned.

[51] Int. Cl.$^6$ .................... A61K 31/70; C07N 17/04
[52] U.S. Cl. .................... 514/25; 514/27; 536/16.8; 536/18.7
[58] Field of Search .............. 514/27, 25; 536/16.8, 536/18.7

[56] References Cited

U.S. PATENT DOCUMENTS

| | | | |
|---|---|---|---|
| 4,623,650 | 11/1986 | Gilligan et al. | 514/312 |
| 4,628,046 | 12/1986 | Labeda et al. | 514/33 |
| 4,746,650 | 5/1988 | Cullen et al. | 514/27 |

OTHER PUBLICATIONS

Morrison et al, Organic Chemistry, 3rd ed, (1973) pp. 181 and 701.

*Primary Examiner*—Elli Peselev
*Attorney, Agent, or Firm*—Peter C. Richardson; Gezina Holtrust; B. Timothy Creagan

[57] ABSTRACT

An antibiotic of the formula

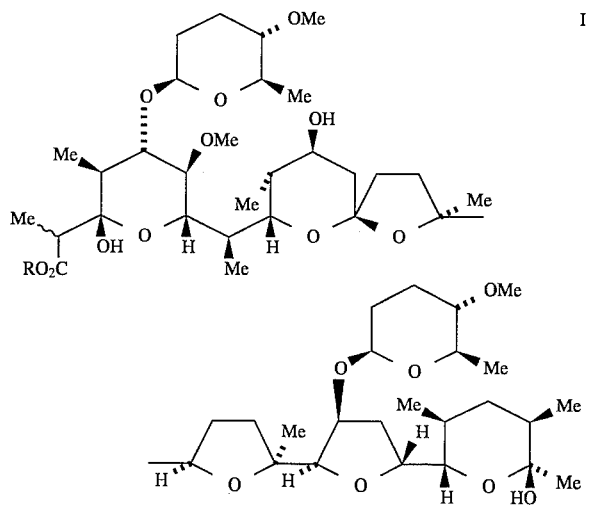

wherein R is hydrogen or a pharmaceutically acceptable cation and Me is methyl.

3 Claims, No Drawings

POLYCYCLIC ETHER ANTIBIOTICS

This is a continuation of application Ser. No. 07/804,482, filed on Dec. 9, 1991, now abandoned.

BACKGROUND OF THE INVENTION

The present invention relates to polycyclic ether antibiotics. This family of antibiotics includes such well known agents as monensin, nigericin, grisorixin, dianemycin, maduramycin, narasin, salinomycin, lasalocid, mutalomycin, ionomycin and leuseramycin. The subject has been reviewed by Westley, "Polyether Antiobiotics", *Adv. Appl. Microbiol.*, 22, 177, 1977.

The polycyclic ether antibiotics listed above are active against Gram-positive bacteria, fungi and protozoa. In particular these antibiotics exhibit potent anti-coccidial activity. They have therefore been employed with varying degrees of success in the treatment of a variety of animal infections.

The protozoan disease, coccidiosis, continues to be a serious problem and its control is of economic importance to veterinary science, especially to the poultry industry. Coccidiosis results from infection by one or more species of *Eimeria* or *Isospora* (for a summary, see Lund and Farr in "Diseases of Poultry," 5th ed., Biester and Schwarte, Eds., Iowa State University Press, Ames, Iowa, 1965, pages 1056–1096). There are six species of coccidia which produce morbidity in susceptible chickens. *Eimeria tenella, E. necatrix, E. brunetti, E. acervulina, E. maxima and E. mivati* produce damage either directly through destruction of epithelial cells of the digestive tract or indirectly through production of toxins. Three other species of protozoa, *E. mitis, E. hagani* and *E. praecox*, belonging to the same genus are considered to be relatively innocuous. However, these species are capable of reducing weight gain, lowering feed efficiency and adversely affecting egg production.

In view of the great economic losses due to coccidiosis, the search for new anticoccidial agents continues.

Enteritis is another disease which can cause severe economic losses to livestock producers. Enteritis occurs in chickens, swine, cattle and sheep and is attributed mainly to anaerobic bacteria, particularly *Clostridium perfringens*, and viruses. Enterotoxemia in ruminants, an example of which is "overeating disease" in sheep, is a condition caused by *C. perfringens* infection.

Swine dysentery is one of the most common swine diseases diagnosed in the United States. Additionally, the disease is prevalent in many other countries and annually causes considerable losses in stock to swine growers around the world. *Treponema hyodysenteriae*, a large spirochete, has been shown to be capable of producing the disease (see Harris, D. L. et al. "Swine Dysentery-1, Inoculation of Pigs with *Treponema hyodysenteriae* (New Species) and Reproduction of the Disease," *Vet. Med/SAC*, 67, 61–64 (1972)) Although it is not known whether *T. hyodysenteriae* is the sole causative organism of swine dysentery, it can be concluded from the data available, that it is a primary source of the infection.

Performance enhancement (increased rate of growth and/or increased efficiency of feed utilization) in ruminants such as cattle, and in monogastric animals such as swine, is another economically desirable objective of veterinary science. Of particular interest is improved performance achieved by increasing the efficiency of feed-utilization. The mechanism for utilization of the major nutritive portion of ruminant feeds is well known. Micro-organisms in the rumen of the animal degrade carbohydrates to produce monosaccharides and then convert these monosaccharides to pyruvate compounds. Pyruvates are metabolized by microbiological processes to form acetates, butyrates or propionates, collectively known as volatile fatty acids. For a more detailed discussion, see Leng in "Physiology of Digestion and Metabolism in the Ruminant," Phillipson et al, Eds., Oriel Press, Newcastle-upon-Tyne, England, 1970, pages 408–410.

The relative efficiency of volatile fatty acid utilization is discussed by McCullough in "Feedstuffs", Jun. 19, 1971, page 19; Eskeland et al. in J. An. Sci., 33, 282 (1971); and Church et al. in "Digestive Physiology and Nutrition of Ruminants", Vol. 2, 1971, pages 622 and 625. Although acetates and butyrates are utilized, propionates are utilized with greater efficiency. Furthermore, when too little propionate is available, animals may develop ketosis. A beneficial compound, therefore, stimulates animals to produce a higher proportion of propionates from carbohydrates, thereby increasing carbohydrate utilization efficiency and also reducing the incidence of ketosis.

The compounds of the present invention may be prepared by alkylation of the acidic polycyclic ether antibiotic designated as UK-58,852 having the formula

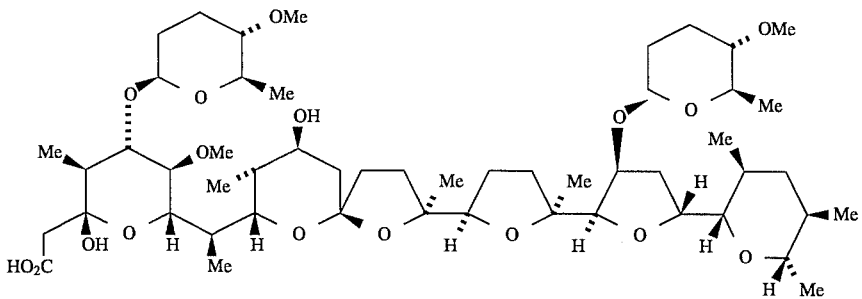

wherein Me is methyl. The antibiotic UK-58,852 is disclosed in European Patent Application Publication No. 0169011. The antibiotic is produced by the submerged aerobic propagation in aqueous nutrient media of the microorganism *Actinomadura roseorufa* Huang sp. nov., ATCC 39697 isolated from a soil sample from Japan.

SUMMARY OF THE INVENTION

The present invention relates to new acidic polycyclic ether antibiotics having the formula:

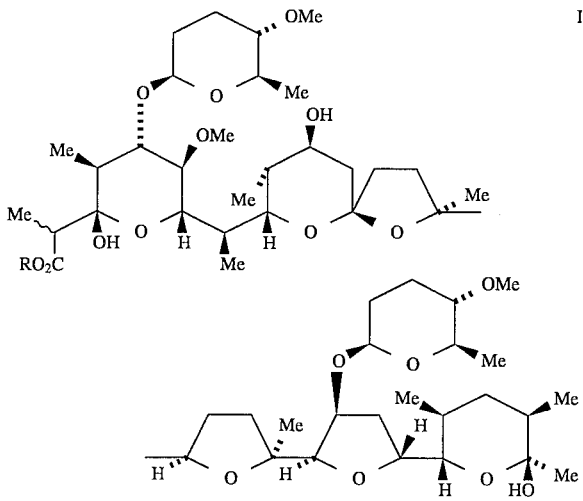

wherein R is hydrogen or a pharmaceutically acceptable cation and Me is methyl.

It will be clear to one skilled in the art that the above formula contemplates two isomers. Both isomers are included within the scope of the present invention.

The present invention also relates to processes for preparing such antibiotics, to pharmaceutical compositions (including those for veterinary use which include animal feeds and drinks) comprising such antibiotics and to methods of using such antibiotics in treating or preventing bacterial fungal or protozoon infections and in promoting growth or increasing the efficiency of feed utilization in animals.

DETAILED DESCRIPTION OF THE INVENTION

A preferred embodiment of the present invention relates to a compound of the formula

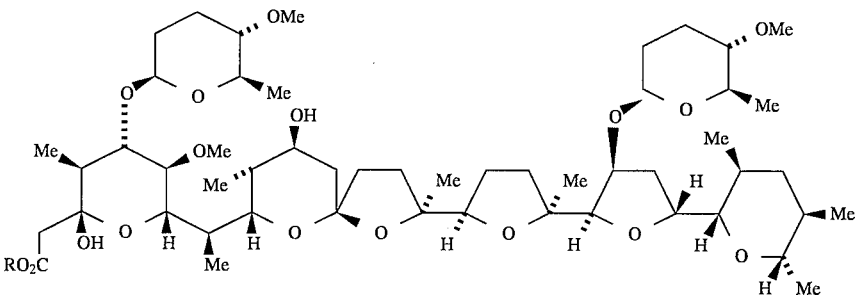

wherein R and Me are as defined above.

The alkylation of UK-58,852 to prepare compounds of the formula I is carried out in tetrahydrofuran containing an alkali metal salt (preferably, the sodium salt) of UK-58,852, in the presence of at least about one molar equivalent of a suitable base. (Preferably sodium hydride or sodium bis(trimethylsilyl)amide), and an excess of a suitable alkylating agent (preferably, iodomethane). The reaction temperature is generally between 5° and 20° C. and the time is preferably about 1 to 2 hours.

Ethyl, propyl, allyl and propargyl analogues of compounds of formula I having antibiotic and growth-promoting activity may be prepared by substituting an appropriate alkylating agent for iodomethane. In a similar manner, alkylation of the antibiotic maduramycin to prepare a compound having antibiotic and growth-promoting activity may also be accomplished.

Another antibiotic that may similarly be alkylated to prepare a compound having antibiotic and growth-promoting activity is UK-61,689 which may be obtained by cleavage of the glycone ring depicted above on the left hand side of UK-58,852.

Efficacy data for the antibiotics of the present invention against coccidial infections in chickens may be obtained in the following fashion: Groups of 3–5 ten-day old pathogen free white leghorn cockerel chicks are fed a mash diet containing the antibiotic to be tested uniformly dispersed therein. After being on this ration for 24 hours, each chick is inoculated per os with oocysts of the particular species of Eimeria being tested. Other groups of 3–5 ten-day old chicks are fed a similar mash diet without an antibiotic of the present invention. They are also infected after 24 hours and serve as infected controls. Yet another group of 3–5 ten-day old chicks is fed the same mash diet without an antibiotic of the present invention and are not infected with coccidia. These serve as normal controls. The results of treatment are evaluated after about five or six days.

The criteria used to measure anticoccidial activity consist of lesion scores of 0 to 4 for *E. tenella* after J. E. Lynch, "A New Method for the Primary Evaluation of Anticoccidial Activity" *Am. J. Vet. Res.*, 22, 324–326 (1961); and 0 to 3 for the other species based on modification of the scoring system devised by J. Johnson and W. H. Reid, "Anticoccidial Drugs Lesion Scoring Techniques in Battery and Floor Pen Experiments in Chicks", *Exp. Parasit.*, 28, 30–36 (1970). A constant ratio is established by dividing the lesion score of each treated group by the lesion score of the infected control.

The performance enhancement value of the antibiotics of the present invention in animal feeds may be determined directly by feeding the animal or by various other techniques. British Patent Specification No. 1,197,826 details an in vitro rumen technique whereby the changes occuring in feed brought about by microorganisms are measured more readily and with great accuracy in the evaluation of animal feeds. This technique involves the use of an apparatus in which the digestive processes of the animals are conducted and studied in vitro. The animal feeds, rumen inoculum and various growth promotants are introduced into and withdrawn from a laboratory unit under carefully controlled conditions and the changes taking place are studied critically and progressively during the consumption of the feed by the microorganisms. An increase in the propionic acid content of the rumen fluid indicates that a desirable response in overall ruminant performance has been brought about by the growth promotant in the feed composition. The change in propionic acid content is expressed as a percent of the propionic acid content found in the control rumen fluid. Long term in vivo feeding studies are used to show a reliable correlation between propionic acid increase in the rumen fluid and improved animal performance.

Rumen fluid is collected from a fistulated cow which is fed on a commercial fattening ration plus hay. The rumen fluid is immediately filtered through cheese cloth, and 10 ml added to a 50 ml conical flask containing 400 mg of standard substrate (68% corn starch+17% cellulose+15% extracted soybean meal), 10 ml of a pH 6.8 buffer and the test compound. The flasks are flushed with oxygen-free nitrogen for about two minutes, and incubated in a shaking water bath at 39° C. for about 16 hours. All tests are conducted in triplicate. After incubation, 5 ml of the sample is mixed with 1 ml of 25% metaphosphoric acid. After 10 minutes, 0.25 ml of formic acid is added and the mixture centrifuged at 1500 rpm for 10 minutes. Samples are then analyzed by gas-liquid chromatography by the method of D. W. Kellog, *J. Dairy Science*, 52, 1690 (1969). Peak heights for acetic, propionic and butyric acids are determined for samples from untreated and treated incubation flasks.

When tested by this in vitro procedure, antibiotics that give rise to increased production of propionic acid over that produced in the control solution without added antibiotic may be considered useful antibiotics. It is known that compounds which stimulate the production of RPA (Rumen propionic acid) improve feed utilization by ruminants such as cattle and sheep, and can also have a similar effect on monogastric animals such as pigs.

The ability of the antibiotics of the present invention to inhibit the growth of various Gram-positive microorganisms may be tested in vitro as follows. Each organism is inoculated in a series of test tubes containing nutrient medium and varying concentrations of antibiotic to determine the minimal concentration of the compound in ug/ml which inhibits the growth of the organism over a period of 24 hours.

The antibiotics of the present invention may be administered to an animal by incorporation into feed compositions, either as the free acid or as a salt e.g., the sodium or potassium salt, or a mixture thereof. Alternatively, a crude form or dried fermentation broth containing an antibiotic of the present invention may be incorporated in a feed composition at the desired potency concentrations. An antibiotic of the present invention may also be administered at the desired dosage using an appropriate sustained release device designed to meter out substantially constant levels of drug.

For use in the treatment of coccidiosis in poultry, including infections due to *Eimeria tenella, E. acervulina, E. maxima, E. brunetti* and *E. necatrix*, the compound of this invention, either as the free acid or as the salt (e.g., the sodium or potassium salt) or a mixture thereof, is administered orally in a suitable carrier. Conveniently, the medication is simply carried in the drinking water or in the poultry feed, so that a therapeutic dosage of the agent is ingested with the daily water or poultry ration. The agent can be directly metered into drinking water, preferably in the form of a liquid, water-soluble concentrate (such as aqueous solution of a water soluble salt) or added directly to the feed, as such, or in the form of a premix or concentrate. A premix or concentrate of therapeutic agent in a carrier is commonly employed for the inclusion of the agent in the feed. Suitable carriers are liquid or solid, as desired, such as water, various meals (for example, soybean oil meal, linseed oil meal, or corncob meal), and mineral mixes such as are commonly employed in poultry feeds. A particularly effective carrier is the poultry feed itself, that is, a small portion of poultry feed. The carrier facilitates uniform distribution of the active materials in the finished feed with which the premix is blended. This is important because only small proportions of the present potent agents are required. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates may be blended by the feed manufacturer with proteinaceous carrier such as soybean oil meal and other meals, as described above, to produce concentrated supplements which are suitable for direct feeding to poultry. In such instances, the poultry are permitted to consume the usual diet. Alternatively, such concentrated supplements may be added directly to the poultry feed to produce a nutritionally balanced, finished feed containing a therapeutically effective level of the compound of this invention. The mixtures are thoroughly blended by standard procedures, such as in a twin shell blender, to ensure homogeneity.

Use levels of the compounds of the present invention will be selected by the veterinary practitioner based on factors such as the activity of the specific compound against the infecting organism and the condition of the animal to be treated.

It will, of course, be obvious to those skilled in the art that the use levels of the compounds described herein will vary under different circumstances. For example, continous low-level medication, during the growing period, that is, during the first 6 to 12 weeks for chickens, is an effective prophylactic measure against coccidial infections. In the treatment of established infections, higher levels may be necessary to overcome the infection.

For prophylactic or therapeutic treatment of chickens to prevent or cure coccidiosis, the use level of a compound of the present invention in feed will generally be in the range of 5 to 30 parts per million (parts by weight). When administered in drinking water, the level will be that which will provide the same daily dose of medication, i.e. 5 to 30 parts per million multiplied by the weight ratio of the average daily consumption of water to the average daily consumption of feed.

For use as a growth promotant in swine, the use level of a compound of the present invention in feed will generally be about 25 parts per million (parts by weight). For use as a growth promotant in cattle, the use level of a compound of the present invention in feed will generally be about 5 parts per million (parts by weight).

The present invention is illustrated by the following non-limiting examples.

EXAMPLE 1

Methyl Analog of UK-58,852

To a 500 mL round bottom flask containing 80 mL of dry tetrahydrofuran (THF) was added 1.12 g (0.028 moles) of sodium hydride (60% dispersion in mineral oil). The solvent was drawn off to remove the mineral oil, and 180 mL of additional THF was introduced. This was followed by the addition of 2.6 mL (5.96 g, 0.042 moles) of iodomethane. The reaction mixture was cooled to 5° C. with an ice bath, and 28.6 g (0.028 moles) of antibiotic UK-58,852 was added in portions as a solid. The reaction mixture was stirred (under nitrogen) and allowed to warm to ambient temperature. The progress of the alkylation was followed by thin layer chromatography (TLC), and after 2 hours maximum product formation was observed. A small volume of water was added and the reaction was concentrated to a hard foam. This material was dissolved in dichloromethane, washed with water and saturated aqueous sodium chloride, and dried over anhydrous sodium sulfate. Purification was accomplished by silica gel chromatography, followed by recrystallization from heptane to give 5.59 g (20%) of the methyl derivative, mp (uncorrected) 194°–195° C.; $[\alpha]_D^{25}$=12.4 (c=0.5, MeOH) C-13 nmr (CDCl$_3$): 180.96, 107.48, 103.16, 102.40, 99.76, 96.87, 86.92, 84.51, 84.21, 82.58, 82.35, 82.06, 80.81, 80.51, 80.21, 79.87, 74.60, 74.37, 72.90, 70.08, 67.61, 67.23, 59.70, 56.78, 56.75, 46.61, 40.83, 39.92, 38.88, 36.46, 33.78, 33.53, 33.18, 32.53, 32.23, 31.79, 31.08, 30.58, 28.92, 27.34, 27.26, 26.92, 25.96, 23.24, 22.60, 18.36, 18.25, 17.44, 16.96, 14.01, 11.58, 11.45, 10.91, 10.29.

Analysis: Calculated for $C_{53}H_{89}O_{18}$·Na: C, 61.38; H, 8.59
Found: C, 61.88; H, 8.69

EXAMPLE 2

The sodium salt of the methyl analog of UK-58,852 was tested for activity against coccidial infections in chickens as described on pages 6–7. When incorporated into the diet of chickens at levels of 5 to 30 parts per million (parts by weight), this compound was found to be effective in controlling infections due to *Eimeria tenella, E. acervulina, E. maxima, E. brunetti* and *E. necatrix*.

What is claimed is:

1. An antibiotic of the formula

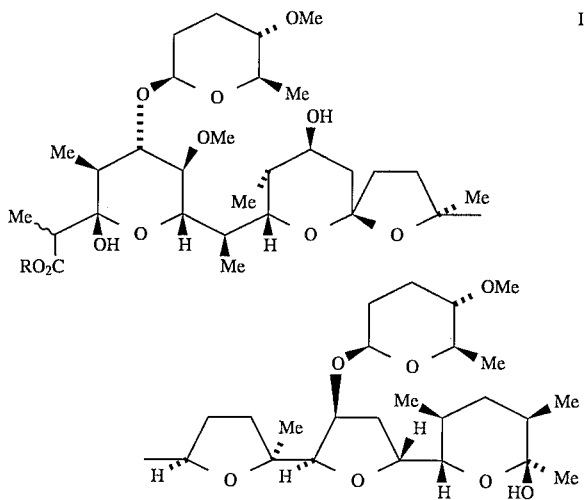

where R is sodium and Me is methyl.

2. A antibiotic pharmaceutical composition comprising an antibiotically effective amount of a compound according to claim 1 and a pharmaceutically acceptable carrier.

3. A method for controlling coccidial infections in poultry comprising administering to said poultry an anti-coccidial amount of a compound of claim 1 effective in treating such a condition.

* * * * *